(12) United States Patent
Schader et al.

(10) Patent No.: US 10,857,307 B2
(45) Date of Patent: Dec. 8, 2020

(54) MEDICAMENT DELIVERY DEVICE AND METHOD FOR ASSEMBLING SAME

(71) Applicant: SANOFI-AVENTIS DEUTSCHLAND GMBH, Frankfurt am Main (DE)

(72) Inventors: Marc Schader, Frankfurt am Main (DE); Axel Teucher, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 373 days.

(21) Appl. No.: 15/552,194

(22) PCT Filed: Feb. 25, 2016

(86) PCT No.: PCT/EP2016/053997
§ 371 (c)(1),
(2) Date: Aug. 18, 2017

(87) PCT Pub. No.: WO2016/135250
PCT Pub. Date: Sep. 1, 2016

(65) Prior Publication Data
US 2018/0036492 A1    Feb. 8, 2018

(30) Foreign Application Priority Data

Feb. 27, 2015 (EP) .................................. 15157001

(51) Int. Cl.
*A61M 5/32* (2006.01)
*A61M 5/20* (2006.01)

(52) U.S. Cl.
CPC ........ *A61M 5/3202* (2013.01); *A61M 5/2033* (2013.01); *A61M 5/321* (2013.01); *A61M 2205/273* (2013.01)

(58) Field of Classification Search
CPC .. A61M 5/3202; A61M 5/2033; A61M 5/321; A61M 2205/273
See application file for complete search history.

(56) References Cited

U.S. PATENT DOCUMENTS

| 5,342,309 A | 8/1994 | Hausser |
| 2008/0103453 A1* | 5/2008 | Liversidge ............ A61M 5/326 604/187 |

(Continued)

FOREIGN PATENT DOCUMENTS

| EP | 0268445 | 5/1988 |
| EP | 2143456 | 1/2010 |

(Continued)

OTHER PUBLICATIONS

International Preliminary Report on Patentability in International Application No. PCT/EP2016/053997, dated Aug. 29, 2017, 6 pages.

(Continued)

*Primary Examiner* — Lauren P Farrar
(74) *Attorney, Agent, or Firm* — Fish & Richardson P.C.

(57) ABSTRACT

The disclosure relates to a medicament delivery device, comprising:
  a tubular body having a distal end,
  a cap adapted to be connected to the distal end (of the body,
wherein the body comprises a first clip having a first stop and a first ramp, wherein the cap comprises a second clip having a second stop and a second ramp, wherein the first ramp and the second ramp are adapted to be mutually engaged when the cap is connected to the body in a first position, wherein the first ramp and the second ramp are adapted to resiliently deflect at least one of the first clip and the second clip when the cap is being moved from the first position towards a second position, wherein in the (Continued)

second position the first stop and the second stop abut each other to prevent the cap from being moved into the first position. Furthermore, the disclosure relates to a method for assembling the medicament delivery device.

20 Claims, 3 Drawing Sheets

(56) References Cited

U.S. PATENT DOCUMENTS

| | | |
|---|---|---|
| 2013/0245564 A1 | 9/2013 | Cheng |
| 2013/0281938 A1* | 10/2013 | Ekman ............... A61M 5/3213 604/198 |
| 2013/0296797 A1* | 11/2013 | Liversidge ............ A61M 5/326 604/198 |
| 2013/0324925 A1 | 12/2013 | Brereton et al. |
| 2014/0243752 A1 | 8/2014 | Hsu et al. |

FOREIGN PATENT DOCUMENTS

| | | |
|---|---|---|
| EP | 2468343 | 6/2012 |
| JP | S63-19564 | 9/1988 |
| WO | WO 2008/050158 | 5/2008 |
| WO | WO 2012/095661 | 7/2012 |
| WO | WO 2014/155536 | 10/2014 |

OTHER PUBLICATIONS

International Search Report and Written Opinion in International Application No. PCT/EP2016/053997, dated Apr. 1, 2016, 8 pages.

\* cited by examiner

US 10,857,307 B2

MEDICAMENT DELIVERY DEVICE AND METHOD FOR ASSEMBLING SAME

CROSS REFERENCE TO RELATED APPLICATIONS

The present application is the national stage entry of International Patent Application No. PCT/EP2016/053997, filed on Feb. 25, 2016, and claims priority to Application No. EP 15157001.7, filed in on Feb. 27, 2015, the disclosures of which are expressly incorporated herein in entirety by reference thereto.

TECHNICAL FIELD

The disclosure relates to a medicament delivery device and to a method for assembling the medicament delivery device.

BACKGROUND

Administering an injection is a process which presents a number of risks and challenges for users and healthcare professionals, both mental and physical. Pre-filled syringes that are filled with a selected dosage of a medicament for administering the medicament to a patient are known in the art. Drug delivery devices comprising a needle sleeve for covering a needle of a pre-filled syringe before and after use are also known. In order to mitigate the risk of cross contamination it is desirable to make users aware if a medicament delivery device has been used or not.

There remains a need for an improved medicament delivery device.

SUMMARY

This disclosure features an improved medicament delivery device and an improved method for assembling a medicament delivery device.

In one aspect, a medicament delivery device comprises:
a tubular body having a distal end,
a cap adapted to be connected to the distal end of the body, wherein the body comprises a first clip having a first stop and a first ramp, wherein the cap comprises a second clip having a second stop and a second ramp, wherein the first ramp and the second ramp are adapted to be mutually engaged when the cap is connected to the body in a first position, wherein the first ramp and the second ramp are adapted to resiliently deflect at least one of the first clip and the second clip when the cap is being moved from the first position towards a second position, wherein in the second position the first stop and the second stop abut each other to prevent the cap from being moved into the first position. This prevents a user from putting back the cap after having removed the cap. Thus, a used or unsterile device can be unambiguously identified.

In an exemplary embodiment the first ramp and the second ramp are arranged to deflect the at least one of the first clip and the second clip in a radial inward direction or a radial outward direction. In another exemplary embodiment the first ramp and the second ramp may be arranged to deflect the at least one of the first clip and the second clip in a different direction, e.g. a tangential direction.

In an exemplary embodiment at least one of the first clip and the second clip is resilient.

In an exemplary embodiment both the first clip and the second clip are resilient, wherein one of the body and the cap comprises or contains a component adapted to radially support the respective one of the first clip and the second clip on said one of the body and the cap. Said supported clip can be deflected prior to assembly of the supporting component allowing initial assembly of the cap to the body. If the supporting component is subsequently assembled said clip cannot be deflected anymore such that the cap cannot be re-attached after removal.

In an exemplary embodiment the first ramp of the first clip on the body is directed substantially radially outward, wherein the component adapted to radially support the first clip is arranged as a needle sleeve arranged within the body. The needle sleeve may be movably arranged within the body for allowing relative movement along a longitudinal axis in a distal direction and/or a proximal direction for exposing or covering an injection needle or for triggering an injection cycle or for unlocking a trigger button when the needle sleeve is pushed against an injection site.

In an exemplary embodiment the body and the cap comprise corresponding spline features allowing to assemble the cap to the body in the second position only in one relative angular position, in which the first clip and the second clip are axially aligned. This ensures that the function preventing the cap form being re-attached to the body cannot be circumvented by a different angular position of the cap relative to the body.

In an exemplary embodiment a circumferential collar with a snap feature is arranged on the distal end of the body, wherein a corresponding snap feature is arranged in a proximal end of the cap.

In an exemplary embodiment the first clip is arranged within an interruption of the circumferential collar.

In an exemplary embodiment the spline feature on the body comprises at least one gap between the circumferential collar and the first clip.

In an exemplary embodiment the spline feature on the cap comprises at least one rib adjacent the second clip and adapted to engage in the at least one gap.

In another spect, a method for assembling the medicament delivery device comprises:
assembling the cap to the distal end of the body in a second position, in which the first stop and the second stop abut each other to prevent the cap from being moved further proximally into a first position,
applying a radially inward directed force to the first clip for axially disengaging the first stop from the second stop,
moving the cap further proximally into the first position and removing the force on the first clip.

This prevents a user from putting back the cap after having removed the cap. Thus, a used or unsterile device can be unambiguously identified.

In an exemplary embodiment after the cap has been moved into the first position and the force on the first clip has been removed a needle sleeve is inserted into the body for radially inwardly supporting the first clip. If the needle sleeve is subsequently assembled said clip cannot be deflected anymore such that the cap cannot be re-attached after removal.

In an exemplary embodiment prior to assembling the cap to the body in the second position the body and the cap are angularly aligned by corresponding spline features such that the first clip and the second clip are axially aligned. This ensures that the function preventing the cap form being re-attached to the body cannot be circumvented by a different angular position of the cap relative to the body.

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE FIGURES

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
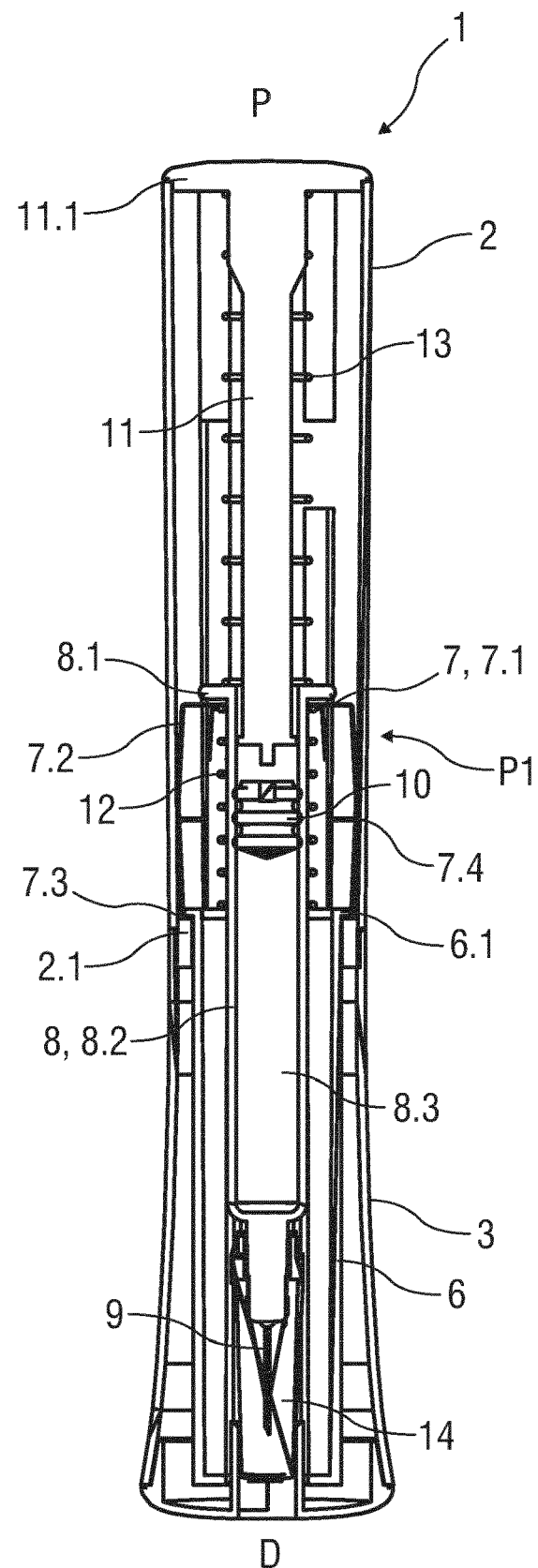
FIG. 1 is a schematic longitudinal section of an exemplary embodiment of a medicament delivery device having a body and a cap.

FIG. 1 is a schematic longitudinal section of an exemplary embodiment of a medicament delivery device 1. The medicament delivery device 1 comprises a substantially elongate and cylindrical body 2 and a cap 3 arrangeable over a distal end of the body 2.

The medicament delivery device 1 furthermore comprises a sleeve 6 with a proximal collar 6.1 movably arranged within the body 2 for allowing relative movement along a longitudinal axis in a distal direction D and/or a proximal direction P.

A syringe carrier 7 for retaining a syringe 8 is arranged within the body 2. The syringe carrier 7 comprises a transverse portion 7.1 adapted to support a proximal flange 8.1 on a syringe barrel 8.2 of the syringe 8 such that the syringe 8 is prevented from moving in the distal direction D relative to the carrier 7. The carrier 7 is movably disposed within the body 2. One or more first legs 7.2 originating from the transverse portion 7.1 of the carrier 7 are directed in the distal direction D. The first leg 7.2 comprises a radially inwardly directed distal first protrusion 7.3 and a radially inwardly directed proximal second protrusion 7.4 adapted to axially abut the collar 6.1 on the sleeve 6 for limiting axial movement of the sleeve 6 relative to the carrier 7. Furthermore, the first leg 7.2 is adapted to distally abut an axial stop 2.1 in the body 2 limiting movement of the carrier 7 in the distal direction relative to the body 2.

The syringe barrel 8.2 is arranged as a hollow cylinder defining a cavity 8.3 for receiving a medicament. A hollow injection needle 9 is arranged at a distal end of the syringe barrel 8.2 in a manner to be in fluid communication with the cavity 8.3. A stopper 10 is disposed within the syringe barrel 8.2 for proximally limiting the cavity 8.3. The stopper 10 may be displaced within the syringe barrel 8.2 for ejecting the medicament from the cavity through the needle 9.

A piston rod 11 is arranged within the body 2 in a manner to engage the stopper 10 for displacing it within the syringe barrel 8.2. In an exemplary embodiment the piston rod 11 is attached to the body 2 preventing relative movement between the piston rod 11 and the body 2. In an exemplary embodiment the piston rod 11 may be integrally shaped with the body 2 or the piston rod 11 may be secured to the body 2 by latches (not illustrated).

A sleeve spring 12 is arranged between the carrier 7 and the sleeve 6 in a manner biasing the sleeve 6 in the distal direction D relative to the carrier 7 such that the collar 6.1 of the sleeve 6 abuts the distal first protrusion 7.3 of the carrier 7.

A syringe spring 13 is arranged over the piston rod 11 between a proximal end face 11.1 of the piston rod 11 and the proximal flange 8.1 of the syringe 8 thus biasing the syringe 8 in the distal direction D relative to the piston rod 11 and body 2.

In an initial state a protective needle sheath 14 is arranged over the needle 9. The cap 3 is adapted to engage the protective needle sheath 14, e.g. by a barb, in manner to remove it from the needle once the cap 3 is removed from the body 2 by pulling it in the distal direction D. A snap feature 2.6 (cf. FIG. 3) may be arranged on the body 2 for snap fitting the cap 3 to the body 2.

Figure 2:
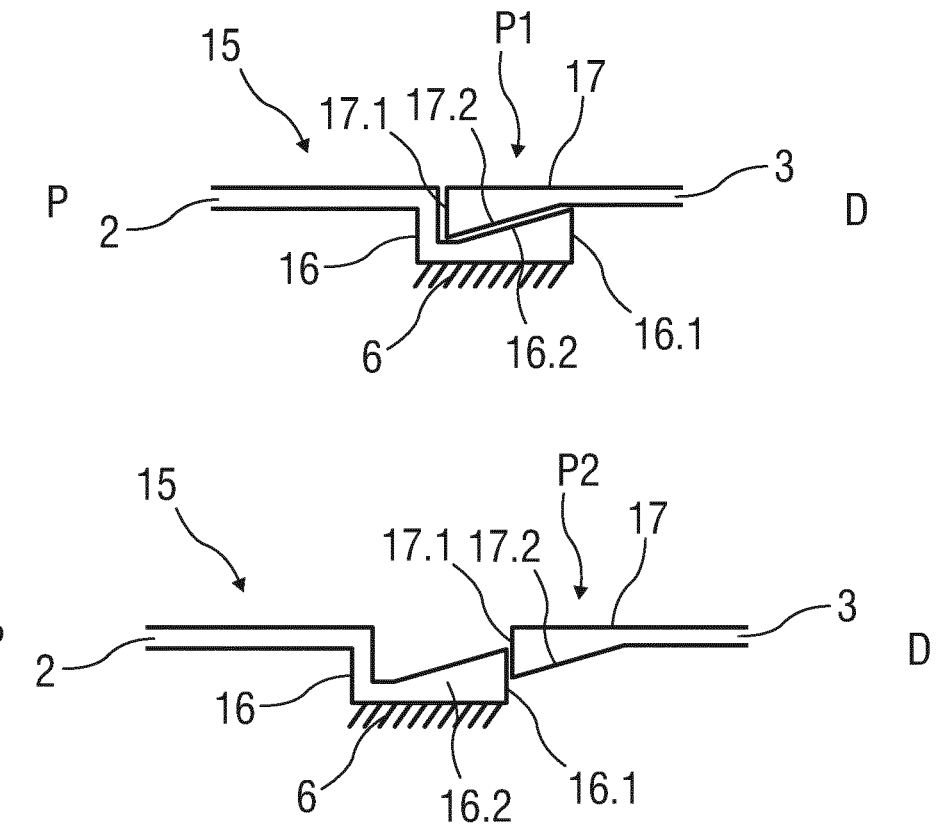
FIG. 2 is a schematic view of an exemplary embodiment of a mechanism for preventing the cap from being reattached to the body after having been removed.

FIG. 2 is a schematic view of an exemplary embodiment of a mechanism 15 for preventing the cap 3 from being reattached to the body 2 after having been removed. The mechanism 15 is shown in two different states. The mechanism 15 comprises a first clip 16 on the body 2, the first clip 16 having a first stop 16.1 and a first ramp 16.2. Furthermore, the mechanism 15 comprises a second clip 17 on the cap 3, the second clip 17 having a second stop 17.1 and a second ramp 17.2, wherein the first ramp 16.2 and the second ramp 17.2 are adapted to be engaged to each other when the cap 3 is connected to the body 2 in a first position P1. When the cap 3 is moved from the first position P1 towards a second position P2 the mutually engaged first ramp 16.2 and second ramp 17.2 resiliently deflect at least one of the first clip 16 and the second clip 17 until the first ramp 16.2 disengages from the second ramp 17.2 in the second position P2 thus allowing the deflected one of the first clip 16 and the second clip 17 to relax such that in the second position P2 the stops axially abut each other to prevent the cap 3 from being moved back into the first position P1.

In an exemplary embodiment the first ramp 16.2 and the second ramp 17.2 are arranged to deflect the at least one of the first clip 16 and the second clip 17 in a radial inward or outward direction. In another non-illustrated exemplary embodiment the first ramp 16.2 and the second ramp 17.2 may be arranged to deflect the at least one of the first clip 16 and the second clip 17 in a different direction, e.g. a tangential direction.

In an exemplary embodiment at least one of the clips 16, 17 is resilient while the other is more rigid. For example, the first clip 16 on the body 2 may be more resilient than the second clip 17 on the cap 3. In another exemplary embodiment both clips 16, 17 are resilient (or at least the cap 3 on which the second clip 17 is arranged is resilient to some extent such that the cap 3 may be pulled off the body 2), wherein one of the body 2 and the cap 3 comprises or contains a component, adapted to radially support the respective clip 16, 17 preventing deflection thereof. In an exemplary embodiment this component may be the sleeve 6 radially inwardly supporting the first clip 16. In this embodiment the first ramp 16.2 of the first clip 16 is directed radially outward. In other non-illustrated embodiments the component may be arranged within the cap 3 for preventing inward deflection of the second clip 17 which would then have a radially outwardly directed second ramp 17.2.

Figure 3:
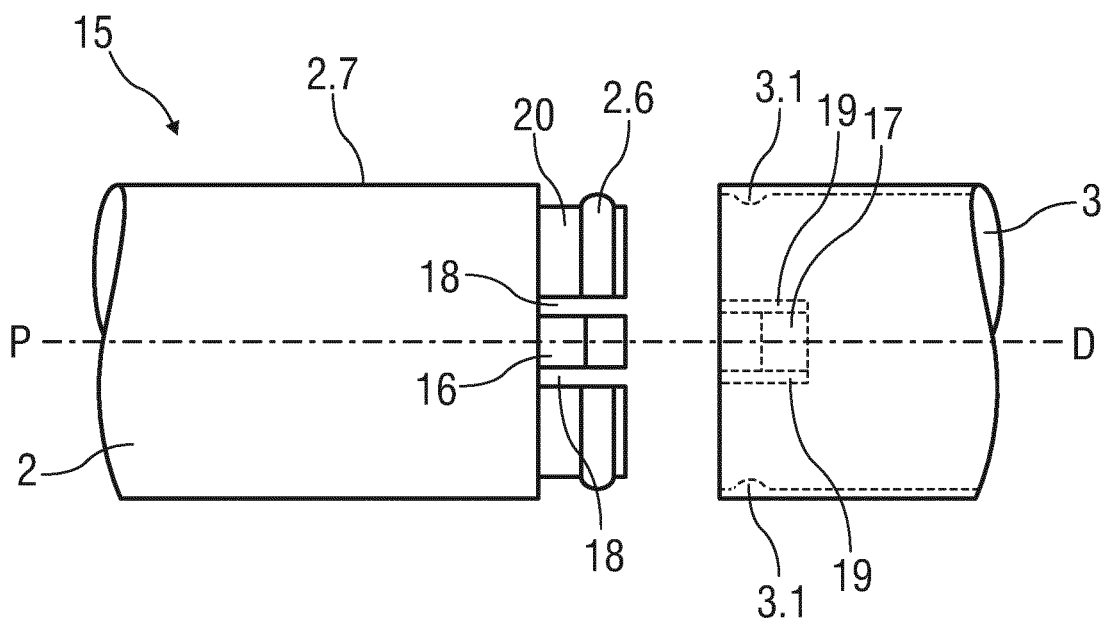
FIG. 3 is a schematic view of a distal end of the body and a proximal end of the cap with the mechanism for preventing the cap from being reattached to the body after having been removed.

FIG. 3 is a schematic view of the distal end 2.7 of the body 2 and a proximal end of the cap 3 with the mechanism 15. The body 2 and the cap 3 comprise corresponding spline features 18, 19 allowing assembly of the cap 3 to the body 2 in the second position P2 only in one relative angular position, in which the first clip 16 of the body 2 and second clip 17 of the cap 3 are axially aligned.

In an exemplary embodiment a circumferential collar 20 with a snap feature 2.6 is arranged on the distal end 2.7 of the body 2, wherein a corresponding snap feature 3.1 is arranged in the proximal end of the cap 3. The first clip 16 is arranged within an interruption of the circumferential collar 20. The spline feature 18 on the body comprises one or more gaps 18 between the circumferential collar 20 and the first clip 16. The spline feature 19 on the cap 3 may comprise one or more rib 19 adjacent the second clip 17 adapted to engage in the at least one gap 18.

Figure 4A:
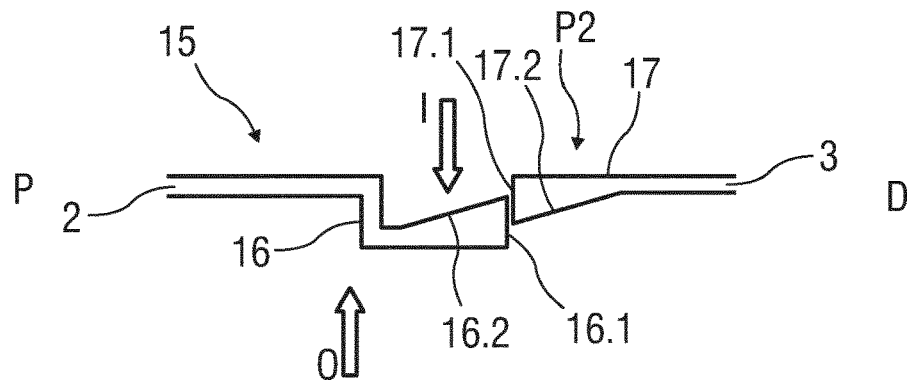
FIG. 4 is schematic view illustrating a method for assembling the medicament delivery device.
Figure 4B:
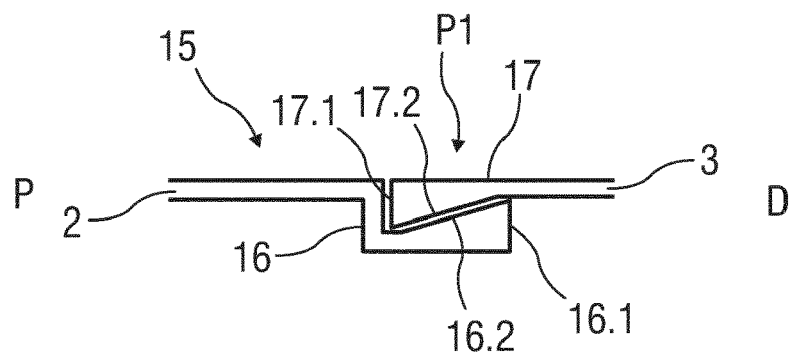
Figure 4C:
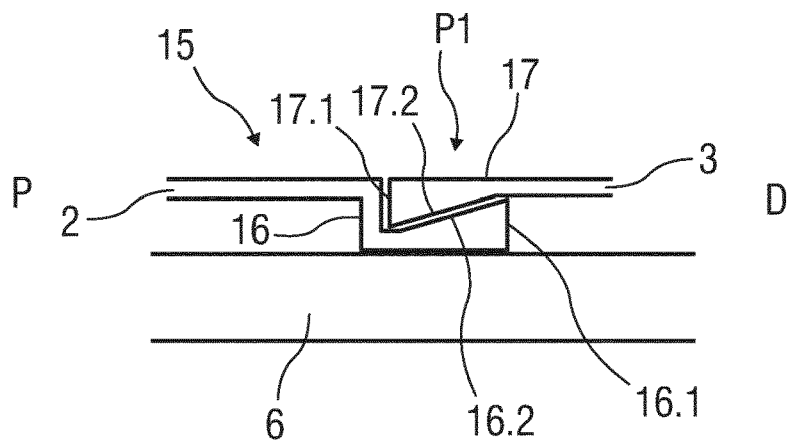

The cap 3 may initially be assembled to the body 2 by a method schematically illustrated in FIGS. 4A to 4C:

In FIG. 4A the cap 3 is assembled to the distal end 2.7 of the body 2 in the second position P2 by moving the cap 3 in the proximal direction P relative to the body 2, such that the first and second stops 16.1, 17.1 abut each other. The cap 3 is hence prevented from being moved further proximally into the first position P1.

A force directed in a radial inward direction I is applied to the first clip 16 on the body 2 for axially disengaging the stops 16.1, 17.1. The cap 3 is then moved further in the proximal direction P into the first position P1 and the force in the radial inward direction I on the first clip 16 is removed such that the first clip 16 relaxes and returns in a radial outward direction 0. The connection between the body 2 and the cap 3 is thus closed and the mechanism 15 arrives in the first position P1 as illustrated in FIG. 4B.

Subsequently, as illustrated in FIG. 4C the needle sleeve 6 is inserted into the body 2 for radially inwardly supporting the first clip 16 such that the first clip 16 cannot be deflected in the radial inward direction I again, e.g. after removing the cap 3 and attempting to replace it.

In an exemplary embodiment prior to assembling the cap 3 to the body 2 in the second position P2 the body 2 and the cap 3 may have to be angularly aligned by the corresponding spline features 18, 19 (cf. FIG. 3), such that the first clip 16 of the body 2 and the second clip 17 of the cap 3 are axially aligned.

Although the mechanism 15 for preventing the cap 3 from being reattached to the body 2 has been described as part of the medicament delivery device 1 illustrated in FIG. 1 the skilled person will understand that the mechanism 15 may be applied with any medicament delivery device regardless of whether it is a fully or partly automatic or manually operated device.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl- ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(w-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys- Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;
or an Exendin-4 derivative of the sequence des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains p and E have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

LIST OF REFERENCES 1 medicament delivery device
2 body
2.1 axial stop
2.6 snap feature
2.7 distal end
3 cap
3.1 snap feature
6 sleeve
6.1 proximal collar
7 syringe carrier
7.1 transverse portion
7.2 first leg
7.3 first protrusion
7.4 second protrusion
8 syringe
8.1 proximal flange
8.2 syringe barrel
8.3 cavity
9 needle
10 stopper
11 piston rod
11.1 proximal end face
12 sleeve spring
13 syringe spring
14 protective needle sheath
15 mechanism
16 first clip
16.1 first stop
16.2 first ramp
17 second clip
17.1 second stop
17.2 second ramp
18 spline feature, gap
19 spline feature
20 circumferential
D distal direction
I radial inward direction
O radial outward direction
P proximal direction
P1 first position
P2 second position

The invention claimed is:

1. A medicament delivery device comprising:
a tubular body having a distal end, the body comprising a first clip having a first stop and a first ramp; and
a cap adapted to be removably connected to the distal end of the body, the cap comprising a second clip having a second stop and a second ramp,
wherein the first ramp and the second ramp are adapted to be mutually engaged when the cap is connected to the body in a first position,
wherein the first ramp and the second ramp are adapted to resiliently deflect at least one of the first clip or the second clip such that one of the first clip or the second clip moves radially away from the other of the first clip or the second clip as the cap is being moved from the first position in a distal direction towards a second position, and
wherein in the second position the first stop and the second stop abut each other to prevent the cap from being moved into the first position.

2. The medicament delivery device according to claim 1, wherein the first ramp and the second ramp are arranged to radially deflect the at least one of the first clip or the second clip.

3. The medicament delivery device according to claim 1, wherein at least one of the first clip or the second clip is resilient.

4. The medicament delivery device according to claim 3, wherein both the first clip and the second clip are resilient, wherein the body or the cap comprises a component adapted to radially support a respective one of the first clip and the second clip on the one of the body or the cap.

5. The medicament delivery device according to claim 4, wherein:
the first ramp of the first clip on the body is directed substantially radially outward, and the component comprises a needle sleeve arranged within the body.

6. The medicament delivery device according to claim 1, wherein the body and the cap comprise corresponding spline features allowing the cap to be assembled to the body in the second position only in one relative angular position in which the first clip and the second clip are axially aligned.

7. The medicament delivery device according to claim 1, wherein:
a circumferential collar with a snap feature is arranged on the distal end of the body, and a corresponding snap feature is arranged in a proximal end of the cap.

8. The medicament delivery device according to claim 7, wherein the first clip is arranged within an interruption of the circumferential collar.

9. The medicament delivery device according to claim 7, wherein:
the body and the cap comprise corresponding spline features allowing the cap to be assembled to the body in the second position only in one relative angular position in which the first clip and the second clip are axially aligned, and
the corresponding spline feature on the body comprises at least one gap between the circumferential collar and the first clip.

10. The medicament delivery device according to claim 9, wherein the corresponding spline feature on the cap comprises a rib adjacent the second clip and adapted to engage in the at least one gap.

11. The medicament delivery device according to claim 1, wherein one of the first clip and the second clip is rigid, and another of the first clip and the second clip is resilient.

12. A mechanism for a medicament delivery device, the mechanism comprising:
a first clip having a first stop and a first ramp; and
a second clip on a cap of the medicament delivery device adapted to be removably connected to a distal end of the medicament delivery device, the second clip having a second stop and a second ramp,
wherein the first ramp and the second ramp are adapted to be mutually engaged when the cap is connected to a body of the medicament delivery device in a first position,
wherein the first ramp and the second ramp are adapted to resiliently deflect at least one of the first clip or the second clip such that one of the first clip or the second clip moves radially away from the other of the first clip or the second clip the cap is being moved from the first position in a distal direction towards a second position,
wherein in the second position the first stop and the second stop abut each other to prevent the cap from being moved into the first position.

13. The mechanism according to claim 12, wherein the first ramp and the second ramp are arranged to radially deflect the at least one of the first clip or the second clip.

14. The mechanism according to claim 12, wherein the first clip or the second clip is resilient.

15. The mechanism according to claim 12, further comprising spline features allowing the cap to be assembled to the body in the second position only in one relative angular position in which the first clip and the second clip are axially aligned.

16. The mechanism according to claim 12, further comprising:
a circumferential collar with a snap feature, and
a corresponding snap feature arranged in a proximal end of the cap.

17. A method for attaching a cap to a tubular body of a medicament delivery device, the body having a distal end, the body comprising a first clip having a first stop and a first ramp, and the cap being adapted to be removably connected to the distal end of the body, the cap comprising a second clip having a second stop and a second ramp, wherein the first ramp and the second ramp are adapted to be mutually engaged when the cap is connected to the body in a first position, wherein the first ramp and the second ramp are adapted to resiliently deflect at least one of the first clip or the second clip such that one of the first clip or the second clip moves radially away from the other of the first clip or the second clip as the cap is being moved from the first position in a distal direction towards a second position, and wherein in the second position the first stop and the second stop abut each other to prevent the cap from being moved into the first position, wherein the method comprises:
placing the cap of the medicament delivery device on the distal end of the body of the medicament delivery device in the second position in which the first stop of the first clip of the body and the second stop of the second clip of the cap abut each other to inhibit the cap from being moved further proximally into the first position;
applying a radially inward directed force to the first clip of the body for axially disengaging the first stop of the first clip from the second stop of the second clip; and
moving the cap further proximally into the first position and removing the force on the first clip, thereby removably attaching the cap to the distal end of the body of the medicament delivery device.

18. The method according to claim 17, further comprising, after moving the cap further proximally into the first position and removing the force on the first clip, causing a needle sleeve to be inserted into the body for radially inwardly supporting the first clip.

19. The method according to claim 17, further comprising, before attaching the cap of the medicament delivery device, removing the cap from the body.

20. The method according to claim 17, wherein attaching the cap to the body comprises causing corresponding spline features of the first clip and the second clip to engage to axially align the first clip and the second clip.

* * * * *

UNITED STATES PATENT AND TRADEMARK OFFICE
CERTIFICATE OF CORRECTION

PATENT NO. : 10,857,307 B2
APPLICATION NO. : 15/552194
DATED : December 8, 2020
INVENTOR(S) : Marc Schader and Axel Teucher Page 1 of 1

It is certified that error appears in the above-identified patent and that said Letters Patent is hereby corrected as shown below:

In the Claims

In Column 11, Line 38, Claim 12, delete "clip" and insert -- clip as --

Signed and Sealed this
Thirtieth Day of March, 2021

Drew Hirshfeld
*Performing the Functions and Duties of the*
*Under Secretary of Commerce for Intellectual Property and*
*Director of the United States Patent and Trademark Office*